United States Patent [19]

Platt

[11] 4,206,644
[45] Jun. 10, 1980

[54] RESPIRATION SENSORS

[75] Inventor: Adam S. Platt, Bushey Heath, England

[73] Assignee: National Research Development Corporation, London, England

[21] Appl. No.: 946,073

[22] Filed: Sep. 26, 1978

[30] Foreign Application Priority Data

Sep. 29, 1977 [GB] United Kingdom ............... 40531/77

[51] Int. Cl.² .......................... G01F 1/68; A61B 5/08
[52] U.S. Cl. ............................ 250/231 P; 128/204.23
[58] Field of Search ............................ 73/194 E, 228; 128/2.07, 2.08, 145.5–145.8, DIG. 29; 137/DIG. 9

[56] References Cited

U.S. PATENT DOCUMENTS

| | | | |
|---|---|---|---|
| 3,265,062 | 8/1966 | Hesse | 128/145.8 |
| 3,680,378 | 8/1972 | Aurilio et al. | 128/2.08 X |
| 3,946,726 | 3/1976 | Pikul | 73/228 X |
| 3,962,917 | 6/1976 | Terada | 128/2.08 X |
| 3,971,253 | 7/1976 | Hini et al. | 73/228 |
| 4,003,255 | 1/1977 | Spencer | 73/194 E |
| 4,041,756 | 8/1977 | Head et al. | 73/194 E |

*Primary Examiner*—Donald Watkins
*Attorney, Agent, or Firm*—Cushman, Darby & Cushman

[57] ABSTRACT

A respiration sensor for use with a medical ventilator, suitably between the patient airway and the Y-piece where the expiratory and inspiratory flows separate, comprises a tube with a flap mounted therein, the flap being resiliently and magnetically biassed to a datum position extending transversely across the tube interior, but the flap being movable in opposite senses from its datum in response to gas flow from the tube, and means for selectively detecting such opposite movements. The flap preferably leaves a gap.

7 Claims, 1 Drawing Figure

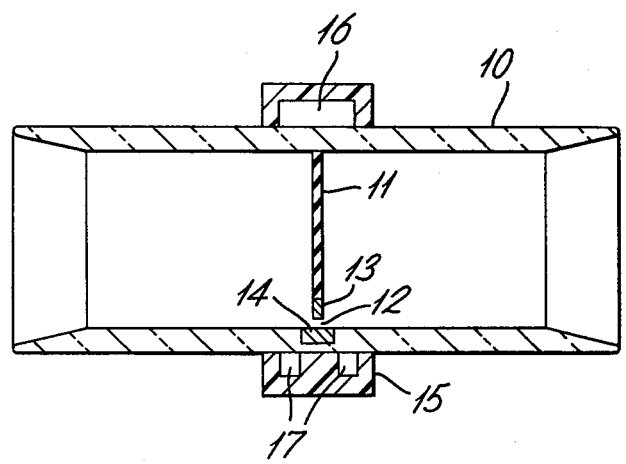

RESPIRATION SENSORS

This invention concerns respiration sensors for use in medical ventilation apparatus, and particularly in such apparatus of a kind which can be operated to augment or assist spontaneous respiration.

Apparatus of the kind just mentioned is open to improvement in the way in which it operates relative to a patient's spontaneous respiration. For example, in a recently proposed new procedure called 'intermittent mandatory ventilation' a patient is allowed to breathe spontaneously while being, in addition, artificially ventilated by a positive pressure ventilator at preselected time intervals. This procedure fails, among other things, to time the artificial ventilation relative to the patient's natural respiration cycle. Another example is the application of continuous positive airway pressure whereby spontaneous inspiration is assisted, but the effort required for spontaneous expiration is increased unless the airway pressure is adjusted at the appropriate times. In each of these examples an improvement can be effected by timing operational events in response to the patient's natural respiration cycle, but there appears to be no commercially-available sensor suited to this purpose.

An object of the present invention is to rectify this omission and there is accordingly provided a respiration sensor for use with medical ventilation apparatus, the sensor comprising a flap mounted along a part of its edge in a tube, the flap being both resiliently and magnetically biassed towards a datum position extending transversely across the interior of the tube, but the flap being movable in opposite senses from the datum position in response to gas flow through the tube, and means for selectively detecting movement of the flap in said opposite senses.

In use the sensor is to be located between the patient's airway and the point in the apparatus where the inspiratory and expiratory gas flow paths separate, such location being in or adjacent to the stem of the apparatus component known usually as the "Y-piece", whereby inspiratory and expiratory flow cause respectively opposite movements of the flap.

Preferred practical requirements for the sensor are that it should be sufficiently sensitive to give rise to flap movement in response to the gas flows resulting spontaneous respiration by a weak patient and offer minimal resistance to such flows, it should operate rapidly to minimise the time taken in attaining optimum airway pressure conditions once a change between inspiration and expiration is detected, and it should be capable of operating independently of the static pressure in the tube. These requirements can be met by the provision of a flap biassing force which is small relative to that caused by respiratory pressure thereon, by making the flap sufficiently light that gravitational forces acting thereon are small relative to the biassing force, and by the provision of a gap between the flap and tube. It is to be noted that the gap will not only allow any slow changes of pressure in the gas flow passages adjacent to the sensor to equalise on both sides of the flap, but will reduce the likelihood of secretions interfering with the flap movement.

The provision of a suitably small biassing force is facilitated by biassing the flap both resiliently and magnetically. The former bias can be provided by the use of a flexible flap at least partly incorporating resilient material to provide an elastic memory inherently biassing the flap towards the desired datum position. Alternatively, the flap can be a hinged rigid member acted upon by a separate bias spring. The magnetic bias can be provided by incorporating magnetisable material in the free edge portion of the flap remote from its mounting in the tube and by incorporating in the tube, or mounting on the tube, a magnet adjacent to the magnetisable material when the flap is at its datum position. Alternatively, the magnetic bias can be provided by interchanging the magnetisable material and magnet, or by the use of two magnets of opposite polarity respectively carried by the flap or tube.

The proposed compound bias is advantageous in comparison to a wholly resilient or magnetic bias because the latter will normally vary as the flap moves away from its datum position and it may therefore be difficult to provide an arrangement which satisfactorily meets all of the above practical requirements. For example, if a wholly resilient bias is adequate to overcome gravitational effects when the flap is in its datum position, too high a respiratory pressure relative to that of a weak patient may be required to move the flap sufficiently to avoid interference with respiratory gas flows. However, since resilient and magnetic bias components will respectively increase and decrease as the flap moves away from its datum position, a compound bias can be more uniform and avoid the difficulty just discussed.

It is proposed at present that the flap-movement detecting means be of photoelectric form including two photocells or other light-responsive devices mounted in or on the tube at opposite sides of the flap, and a lamp or other light source mounted diametrically opposite to the devices. An opaque flap is employed so that its movement progressively masks one or other of the devices relative to the light source, and the consequently varied device output can be used to trigger an appropriate change in airway pressure conditions by way of solenoid-controlled valves or similar controls. The sensitivity of operation is adjustable by altering the thresholds, relative to the device outputs, at which trigger actions occur.

Such detection means are suitably provided in a form which is separably mounted around the tube of a sensor in which the tube terminates in conventional connectors and is, together with the flap, made of sterilisable material. This facilitates use of the proposed sensor.

An indication of the capability of a sensor according to the invention is given by the fact that an initial embodiment using a resilient flap with a steel member embedded therein and used with photocell detectors operates satisfactorily in response to gas flows at respiratory pressure as slow as about 2 mm of mercury.

The accompanying drawing schematically illustrates a presently preferred form of the invention and serves as an example to afford a clearer understanding of the invention.

In the drawing a transparent tube 10 has mounted within its interior a flap 11, the flap being mounted along part of its edge to extend transversely across the tube. The flap does not extend wholly across the tube and so leaves a gap which is denoted at 12. The flap is made of opaque resilient material inherently biassed towards the illustrated datum position extending across the tube perpendicularly to the tube axis. The flap has a member 13 embedded in its edge portion remote from its mounting, and the tube carries adjacent thereto a member 14, these members being respectively magnetisable or magnetic to provide a magnetic bias urging the flap towards its datum position.

The structure so far described is wholly sterilisable, and the tube is formed with tapers or other means at its ends for connection of the tube between the patient airway tube and socalled Y-piece of a medical ventilator.

A yoke 15 is detachably mounted on the tube exterior, this yoke carrying at one end a light source 16 positioned adjacent to the flap-tube mounting, and a pair of photocells 17 positioned diametrically opposite to the light source and on respectively opposite sides of the flap.

The operation of the illustrated apparatus is evident from the earlier description, with gas flows due to inspiration and expiration causing movement of the flap from its datum position in opposite senses, and with such movements being differentially detected by the photocells by masking thereof from the light source by the flap.

While the invention has been described above largely with reference to a presently preferred form, it is clearly capable of variation. For example other forms of flap-movement detection means than opto-electrical are possible, and one such form may involve the detection of differential pressures across the flap which will result in flap movement.

I claim:

1. A respiration sensor for use with medical ventilation apparatus, comprising a flap mounted along a part of its edge in a tube, the flap being both resiliently and magnetically biassed towards a datum position extending transversely across the interior of the tube, said flap being movable in opposite senses from the datum position in response to gas flow through the tube, and means for selectively detecting movement of the flap in said opposite senses wherein the mass of said flap is such that gravitational forces acting thereon are small relative to those of said bias, said bias forces are small relative to those resulting from respiratory pressures on said flap, and there is a gap between said flap and tube.

2. A sensor according to claim 1 wherein said flap is flexible and at least partly incorporates resilient material to provide said resilient bias.

3. A sensor according to claim 1 wherein said flap is made of rigid material acted on by a separate bias spring to provide said resilient bias.

4. A sensor according to claim 1 wherein said flap and tube respectively carry, at mutually adjacent portions thereof remote from the flap-tube mounting when the flap is in its datum position, different ones of two materials which are respectively magnetic and magnetisable to provide said magnetic bias.

5. A sensor according to claim 1 wherein said flap and tube carry, at mutually adjacent portions thereof remote from the flap-tube mounting when the flap is in its datum position, respective magnets of opposite polarity to provide said magnetic bias.

6. A sensor according to claim 1 wherein said movement detecting means is of photoelectric form including a light source for projecting light across the interior of said tube along two paths on opposite sides of said flap when in said datum position, and two light responsive means opposed to said light source along respective ones of said paths, said flap being opaque to interrupt said paths respectively upon movement in opposite senses from said datum position.

7. A sensor according to claim 1 wherein said movement detecting means is responsive to differential pressures across said flap which will result in movement thereof.

* * * * *